US00PP35640P2

(12) United States Plant Patent
Schoone

(10) Patent No.: US PP35,640 P2
(45) Date of Patent: Feb. 6, 2024

(54) ***PHALAENOPSIS* PLANT NAMED 'ESCAPADES'**

(50) Latin Name: *Phalaenopsis hybrida*
Varietal Denomination: Escapades

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/214,521

(22) Filed: Jun. 26, 2023

Related U.S. Application Data

(60) Provisional application No. 63/355,878, filed on Jun. 27, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'Escapades', characterized by its upright plant habit; moderately vigorous to vigorous growth habit; strong flowering stems; strong leaves; freely flowering habit with typically two inflorescences per plant, each inflorescence with numerous flowers; large white-colored flowers with reddish purple-colored blotches; flowers with white, yellow and dark purple-colored labella; and good postproduction longevity.

1 Drawing Sheet

Figure 1:
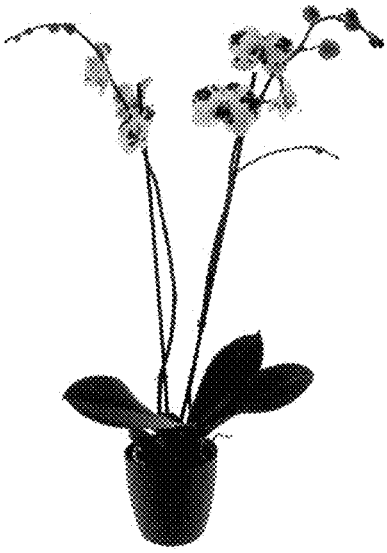

Botanical designation: *Phalaenopsis hybrida.*
Cultivar denomination: 'ESCAPADES'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Aug. 15, 2022, application number 2022/1912. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Escapades'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in March, 2013 in Assendelft, The Netherlands of *Phalaenopsis hybrida* 'Gan Lin Diamond', not patented, as the female, or seed, parent with *Phalaenopsis hybrida* 'Garlin Mary', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in January, 2019.

Asexual reproduction of the new *Phalaenopsis* plant by in vitro meristem propagation in a controlled environment in Assendelft, The Netherlands since January, 2020 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Escapades'. These characteristics in combination distinguish 'Escapades' as a new and distinct *Phalaenopsis* plant:

1. Upright plant habit.
2. Moderately vigorous to vigorous growth habit.

3. Strong flowering stems.
4. Strong leaves.
5. Freely flowering habit with typically two inflorescences per plant, each inflorescence with numerous flowers.
6. Large white-colored flowers with reddish purple-colored blotches.
7. Flowers with white, yellow and dark purple-colored labella.
8. Good postproduction longevity.

Plants of the new *Phalaenopsis* can be compared to plants of the female parent, 'Gan Lin Diamond'. Plants of the new *Phalaenopsis* differ primarily from plants of 'Gan Lin Diamond' in flower petal color as flower petals of plants of the new *Phalaenopsis* are white in color with reddish purple-colored blotches whereas the flower petals of plants of the 'Gan Lin Diamond' are violet in color with purple-colored blotches. In addition, the flower petals of plants of the new *Phalaenopsis* are close to imbricate whereas the flower petals of plants of 'Gan Lin Diamond' are "free" and not imbricate.

Plants of the new *Phalaenopsis* can be compared to plants of the male parent, 'Garlin Mary'. Plants of the new *Phalaenopsis* differ primarily from plants of 'Garlin Mary' in flower petal color as flower petals of plants of the new *Phalaenopsis* are white in color with reddish purple-colored blotches whereas the flower petals of plants of the 'Garlin Mary' are white in color without any blotches.

Plants of the new *Phalaenopsis* can be compared to plants of *Phalaenopsis hybrida* 'Spilled Ink', not patented. In side-by-side comparisons, plants of the new *Phalaenopsis* differ primarily from plants of 'Spilled Ink' in flower petal color as flower petals of plants of the new *Phalaenopsis* have fewer blotches than flower petals of plants of the 'Spilled Ink'. In addition, flowers of plants of the new *Phalaenopsis* have longer cirrhose tips than flowers of plants of 'Spilled Ink'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph at the top of the sheet (FIG. 1) is a side perspective view of a typical flowering plant of 'Escapades' grown in a container.

Figure 2:
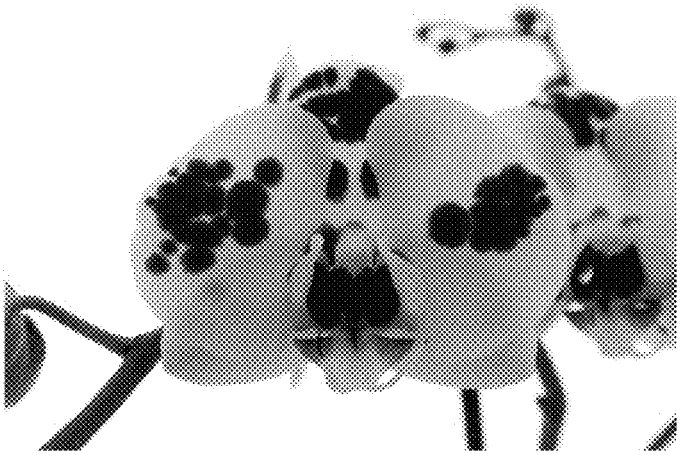

The photograph at the bottom of the sheet (FIG. 2) is a close-up view of typical flowers of 'Escapades'.

DETAILED BOTANICAL DESCRIPTION

The aforementioned photographs and following observations and measurements describe plants grown during the autumn and winter in 10-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27 C. During the final six months of production of the plants, day temperatures ranged from 20 C to 22 C and night temperatures ranged from 18 C to 20 C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Escapades'.

Parentage:

*Female, or seed, parent.*—*Phalaenopsis hybrida* 'Gan Lin Diamond', not patented.

*Male parent.*—*Phalaenopsis hybrida* 'Garlin Mary', not patented.

Propagation:

*Type.*—By in vitro meristem propagation.

*Time to initiate roots, summer and winter.*—About two weeks at temperatures about 28 C to 30 C.

*Time to produce a rooted young plant, summer and winter.*—About 20 to 25 weeks at temperatures about 28 C to 30 C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane.*—About 19.3 cm.

*Plant height, substrate level to top of inflorescences.*—About 56 cm.

*Plant diameter or spread.*—About 37.8 cm.

Leaf description:

*Arrangement and quantity.*—Distichous, simple; sessile; about three leaves per plant.

*Length.*—About 22.6 cm.

*Width.*—About 7.8 cm.

*Aspect.*—Outwardly arching.

*Shape.*—Narrowly obovate; slightly carinate.

*Apex.*—Unequal and broadly acute.

*Base.*—Sheathing. Sheath length: About 1.8 cm. Sheath width: About 1.5 cm. Sheath color: Close to 143A; towards the center, close to 143B.

*Margin.*—Entire; not undulate.

*Texture and luster, upper and lower surfaces.*—Smooth, glabrous; moderately glossy.

*Venation pattern.*—Camptodromous.

*Color.*—Developing leaves, upper surface: Darker than a blend of 139A and 147A. Developing leaves, lower surface: Close to NN137B. Fully expanded leaves, upper surface: Close to a blend of NN137A and 146A; venation, close to NN137A to NN137B. Fully expanded leaves, lower surface: Close to a blend of 146A and 147B; venation, close to 143A.

Inflorescence description:

*Appearance and flowering habit.*—Showy zygomorphic flowers arranged on axillary simple or branched racemes; typically two inflorescences per plant; each inflorescence with about twelve flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about ten weeks on the plant; flowers not persistent.

*Inflorescence length* (*lowermost flower to inflorescence apex*).—About 28.4 cm.

*Inflorescence width*.—About 19.5 cm.

*Flower buds*.—Height: About 1.8 cm. Diameter: About 1.5 cm by 1.7 cm. Shape: Broadly ovate. Color: Close to 144C; upper surface, slightly blotched with close to 152C; towards the base, close to N186B.

*Flower size*.—About 8.2 cm (vertical) by 8.9 cm (horizontal).

*Flower depth*.—About 4.3 cm.

*Petals, quantity and arrangement*.—Three, two lateral petals and one center petal transformed into a labellum.

*Lateral petals*.—Length: About 4.5 cm. Width: About 5.8 cm. Shape: Roughly reniform to lunate. Apex: Obtuse to rounded. Margin: Entire; slightly and finely undulate. Texture and luster, upper and lower surfaces: Smooth, glabrous, velvety; matte. Color: When opening, upper surface: Close to NN155B; towards the base, close to N80A; large blotches, close to N79C and 187A. When opening, lower surface: Close to a blend of 155C and 157D; towards the base, close to 157C; blotches from upper surface visible, close to N79C. Fully opened, upper surface: Close to NN155D; towards the base, close to N78A and N80B; large blotches, close to N78B, and N78C; color does not change with subsequent development. Fully opened, lower surface: Close to NN155D; blotches from upper surface visible, close to N79C; color does not change with subsequent development.

*Labella*.—Appearance: Three-parted with two lateral lobes and a central lobe. Length, lateral lobes: About 2.4 cm. Width, lateral lobes: About 1.8 cm. Length, central lobe: About 2.5 cm. Width, central lobe: About 8 mm to 25 mm. Length, Cirrhose tips: About 1.5 cm. Shape, lateral lobes: Broadly obovate. Shape, central lobe: Deltoid with a slightly elongated apex. Apex, lateral lobes: Obtuse. Apex, central lobe: Acute with two curved cirrhose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3 mm in length, about 5 mm in width and about 7 mm in height. Color: When opening, upper surface: Lateral lobes: Close to NN155D; towards the base, close to 187A and 187B; lower margins, close to 4A. Central lobe: Close to 162C; center, tinged with close to 154D; towards the apex, close to NN155D; towards the base, close to N155A; fine dots, close to 182A; cirrhose tips, close to NN155D with apices, close to N186C and N186D. Callosities: Close to 166A. When opening, lower surface: Lateral lobes: Close to NN155D; towards the base, close to N187C; lower margins, close to 1A and 1B. Central lobe: Close to 154D; towards the apex, close to 145D; towards the base, close to 156B; fine dots, close to 178A; cirrhose tips, close to NN155D with apices, close to N186C and N186D. Fully opened, upper surface: Lateral lobes: Close to NN155D; towards the base, close to 187A and 187B; lower margins, close to 7A to 7B. Central lobe: Close to 162B; towards the apex, close to NN155D; towards the base, close to N155A; fine dots, close to 182A; cirrhose tips, close to NN155D with apices, close to N186C and N186D. Callosities: Close to 166A. Fully opened, lower surface: Lateral lobes: Close to NN155D; towards the base, close to N187C; lower margins, close to 5A. Central lobe: Close to 160C; towards the apex, close to NN155D; towards the base, close to 156B; fine dots, close to 178A; cirrhose tips, close to NN155D with apices, close to N186C and N186D.

*Sepals*.—Quantity and arrangement: Three, one upper dorsal sepal and two lower lateral sepals. Length, dorsal sepal: About 4.5 cm. Width, dorsal sepal: About 3.5 cm. Length, lateral sepals: About 4.6 cm. Width, lateral sepals: About 3.2 cm. Shape, dorsal sepal: Broadly elliptic. Shape, lateral sepals: Ovate. Apex, dorsal and lateral sepals: Obtuse. Base, dorsal and lateral sepals: Truncate. Margin, dorsal and lateral sepals: Entire. Texture and luster, dorsal and lateral sepals, upper surface: Smooth, glabrous, moderately velvety; matte. Texture and luster, dorsal and lateral sepals, lower surface: Smooth, glabrous, slightly velvety; slightly glossy. Color, dorsal sepal: When opening, upper surface: Close to NN155B; towards the base, close to N80A; large blotches, close to N79C and 187A. When opening, lower surface: Close to 145B; towards the apex and margins, close to 150D; large blotches on upper surface visible, close to N79C. Fully opened, upper surface: Close to NN155D; towards the base, close to N78C, N78D and NN78A; heavily blotched and marbled, close to 60A and N79A to N79C; color does not change with subsequent development. Fully opened, lower surface: Close to N155B; towards the base, close to 157D; towards the margins, heavily blotched, close to 71A and N79C; venation, close to N186D; color does not change with subsequent development. Color, lateral sepals: When opening, upper surface: Close to NN155B; lower half, close to 157B and 157C; at the base, close to N80A; large blotches, close to N79C and 187A. When opening, lower surface: Close to 145B; towards the apex and margins, close to 150D; large blotches on upper surface visible, close to N79C. Fully opened, upper surface: Close to 157D; towards the base, close to 157B; heavily blotched and marbled, close to 71A, N79B, N79C and 186D; color does not change with subsequent development. Fully opened, lower surface: Close to 75D and 157A; towards the base, close to N170D; heavily blotched, close to N186D; color does not change with subsequent development.

*Peduncles*.—Length: About 65 cm. Diameter: About 6 mm. Strength: Strong. Aspect: Upright to outwardly arching. Texture and luster: Smooth, glabrous; matte. Color: Close to 146A to 146B; moderately to densely covered with fine dots and marbling, close to 138B.

*Pedicels*.—Length: About 3.1 cm. Diameter: About 3.5 mm. Strength: Moderately strong. Aspect: About 65 degrees from peduncle axis. Texture and luster: Smooth, glabrous; matte. Color: Upper surface:

Close to 145B; proximally, close to 144A. Lower surface: Close to N186C; occasionally sparsely marbled and striped with close to 187B.

*Reproductive organs*.—Androecium: Column length: About 1 cm. Column width: About 7 mm. Column color: Close to NN155B; towards the base, close to 70A to 70B. Pollinia quantity: Two. Pollinia diameter (per two pollinia): About 3 mm. Pollinia color: Close to 24A. Gynoecium: Stigma length: About 4 mm. Stigma width: About 5 mm. Stigma shape: Reniform. Stigma color: Close to 146D. Ovary length: About 1.5 cm. Ovary diameter: About 1 mm. Ovary color: Close to 147C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40C and are suitable for USDA Hardiness Zones 10 to 12.

It is claimed:

1. A new and distinct *Phalaenopsis* plant named 'Escapades' as illustrated and described.

* * * * *